(12) United States Patent
Luo et al.

(10) Patent No.: US 10,054,590 B2
(45) Date of Patent: Aug. 21, 2018

(54) USE OF NUCLEOLIN AS A BIOMARKER FOR LYMPHANGIOGENESIS IN A CANCER PROGNOSIS AND THERAPY

(71) Applicants: Tsinghua University, Beijing (CN); Protgen Ltd., Beijing (CN)

(72) Inventors: Yongzhang Luo, Beijing (CN); Wei Zhuo, Beijing (CN); Yan Fu, Beijing (CN); Guodong Chang, Beijing (CN)

(73) Assignees: Tsinghua University, Beijing (CN); Protgen Ltd., Beijing (CN)

( * ) Notice: Subject to any disclaimer, the term of this patent is extended or adjusted under 35 U.S.C. 154(b) by 0 days.

(21) Appl. No.: 13/962,522

(22) Filed: Aug. 8, 2013

(65) Prior Publication Data

US 2014/0037655 A1  Feb. 6, 2014

Related U.S. Application Data

(63) Continuation of application No. 13/554,913, filed on Jul. 20, 2012, now abandoned.

(60) Provisional application No. 61/510,666, filed on Jul. 22, 2011.

(51) Int. Cl.
  *G01N 33/574* (2006.01)
  *C07K 16/28* (2006.01)
  *A61K 38/39* (2006.01)

(52) U.S. Cl.
  CPC ........... *G01N 33/574* (2013.01); *C07K 16/28* (2013.01); *A61K 38/39* (2013.01); *C07K 2317/76* (2013.01); *G01N 2333/515* (2013.01); *G01N 2800/52* (2013.01); *G01N 2800/56* (2013.01); *G01N 2800/7014* (2013.01)

(58) Field of Classification Search
  None
  See application file for complete search history.

(56) References Cited

U.S. PATENT DOCUMENTS 7,541,150 B2   6/2009 Miller et al.
2009/0191224 A1*  7/2009 Luo et al. .................. 424/178.1

OTHER PUBLICATIONS

Fukumoto et al. (Clinical &Experimental Metastasis (2005) 22: 31-38).*
Shayan, R. et al., "Lymphatic vessels in cancer metastasis: bridging the gaps." *Carcinogenesis* 27(9), 2006, 1729-1738.
Zhuo, W. et al., "Endostatin inhibits tumour lymphangiogenesis and lymphatic metastasis via cell surface nucleolin on lymphangiogenic endothelial cells." *J. Pathol.* 222, 2010, 249-260.

\* cited by examiner

*Primary Examiner* — James H Alstrum-Acevedo
*Assistant Examiner* — Tara L Martinez
(74) *Attorney, Agent, or Firm* — Drinker Biddle & Reath LLP

(57) ABSTRACT

The present invention relates to a method of identifying cancer subjects, in particular human patients, who are suitable for anti-lymphangiogenesis therapy to prevent tumor growth and tumor metastasis. The present invention also relates to a new approach, which uses nucleolin as a bait to search and screen for lymphangiogenesis inhibitors or cancer suppressors, which function in a manner that is analogous to endostatin. The invention is based upon the discovery that nucleolin is specifically expressed on lymphangiogenic vessels and functions as a specific receptor for endostatin, and thus is involved in the signal transduction pathway of endostatin as an anti-lymphangiogenesis inhibitor. The present invention also discloses that cell surface nucleolin on lymphatic endothelial cells is a biomarker for lymphangiogenic vessels, which could be used for the prediction of tumor metastasis.

18 Claims, 18 Drawing Sheets

USE OF NUCLEOLIN AS A BIOMARKER FOR LYMPHANGIOGENESIS IN A CANCER PROGNOSIS AND THERAPY

RELATED APPLICATIONS

This application is a continuation application of U.S. application Ser. No. 13/554,913, filed Jul. 20, 2012, which claims priority to U.S. Provisional Patent Application No. 61/510,666, filed Jul. 22, 2011, the entire content of which is incorporated herein by reference.

FIELD OF THE INVENTION

The present invention relates to a method of identifying cancer subjects, in particular human patients, who are suitable for anti-lymphangiogenesis therapy to prevent tumor growth and tumor metastasis. The present invention also relates to a new approach, which uses nucleolin as a bait to search and screen for lymphangiogenesis inhibitors or cancer suppressors, which function in a manner that is analogous to endostatin. The invention is based upon the discovery that nucleolin is specifically expressed on lymphangiogenic vessels and functions as a specific receptor for endostatin, and thus is involved in the signal transduction pathway of endostatin as an anti-lymphangiogenesis inhibitor. The present invention also discloses that cell surface nucleolin on lymphatic endothelial cells is a biomarker for lymphangiogenic vessels, which could be used for the prediction of tumor metastasis.

BACKGROUND OF THE INVENTION

Endostatin is a 20-kDa proteolytic fragment of collagen XVIII [O'Reilly M S, Boehm T, Shing Y, et al. Endostatin: an endogenous inhibitor of angiogenesis and tumor growth. Cell 1997; 88: 277-285.]. It specifically inhibits the proliferation and migration of vascular endothelial cells, and induces the apoptosis of vascular endothelial cells [Yamaguchi N, Anand-Apte B, Lee M, et al. Endostatin inhibits VEGF-induced endothelial cell migration and tumor growth independently of zinc binding. EMBO J. 1999; 18: 4414-4423]. Furthermore, endostatin efficiently inhibits angiogenesis and tumor growth with low toxicity and no drug resistance [Boehm T, Folkman J, Browder T, et al. Antiangiogenic therapy of experimental cancer does not induce acquired drug resistance. Nature 1997; 390: 404-407,4; Herbst R S, Hess K R, Tran H T, et al. Phase I study of recombinant human endostatin in patients with advanced solid tumors. J Clin Oncol 2002; 20: 3792-3803]. Treatment of endothelial cells with endostatin leads to a variety of downstream effects related to angiogenesis [Abdollahi A, Hahnfeldt P, Maercker C, et al. Endostatin's antiangiogenic signaling network. Mol Cell 2004; 13: 649-663].

Many proteins including integrins, glypicans, laminin, tropomyosin, caveolin, VEGFR-1, VEGFR-2, and MMP2 have been reported to interact with endostatin and may serve as potential endostatin receptors [Rehn M, Veikkola T, Kukk-Valdre E, et al. Interaction of endostatin with integrins implicated in angiogenesis. Proc Natl Acad Sci USA 2001; 98: 1024-1029; MacDonald N J, Shivers W Y, Narum D L, et al. Endostatin binds tropomyosin. A potential modulator of the antitumor activity of endostatin. J Biol Chem 2001; 276: 25190-25196; Karumanchi S A, Jha V, Ramchandran R, et al. Cell surface glypicans are low-affinity endostatin receptors. Mol Cell 2001; 7: 811-822; Sasaki T, Fukai N, Mann K, et al. Structure, function and tissue forms of the C-terminal globular domain of collagen XVIII containing the angiogenesis inhibitor endostatin. EMBO J 1998; 17: 4249-4256; Kim Y M, Jang J W, Lee O H, et al. Endostatin inhibits endothelial and tumor cellular invasion by blocking the activation and catalytic activity of matrix metalloproteinase. Cancer Res 2000; 60: 5410-5413]. Recently, our previous discovery disclosed that cell surface nucleolin functions as a receptor for endostatin [Shi H, Huang Y, Zhou H, et al. Nucleolin is a receptor that mediates antiangiogenic and antitumor activity of endostatin. Blood 2007; 110: 2899-2906]. It specifically locates on angiogenic blood vessels and mediates the anti-angiogenic and anti-tumor activities of endostatin. Moreover, the expression of nucleolin on the cell surface of endothelial cells can be induced by the treatment of VEGF and extracellular matrix and is mediated by intracellular nonmuscle myosin heavy chain 9 [Huang Y, Shi H, Zhou H, et al. The angiogenic function of nucleolin is mediated by vascular endothelial growth factor and nonmuscle myosin. Blood 2006; 107: 3564-3571]. Besides, nucleolin was firstly identified as a major nucleolus protein and has been demonstrated to play a critical and fundamental role in cell growth and proliferation [Srivastava M, Pollard H B. Molecular dissection of nucleolin's role in growth and cell proliferation: new insights. FASEB J 1999; 13: 1911-1922]. It was reported that nucleolin can shuttle to cytoplasma and membrane from the nucleolus [Borer R A, Lehner C F, Eppenberger H M, et al. Major nucleolar proteins shuttle between nucleus and cytoplasm. Cell 1989; 56: 379-390]. Nucleolin expressed on the cell surface is characterized as a biomarker of angiogenic endothelial cells [Christian S, Pilch J, Akerman M E, et al. Nucleolin expressed at the cell surface is a marker of endothelial cells in angiogenic blood vessels. J Cell Biol 2003; 163: 871-878].

The lymphatic system plays important roles in maintaining fluid balance in the body and the pathogenesis of many diseases, including chronic inflammation and cancer [Swartz M A. The physiology of the lymphatic system. Adv Drug Deliv Rev 2001; 50: 3-20; Baluk P, Tammela T, Ator E, et al. Pathogenesis of persistent lymphatic vessel hyperplasia in chronic airway inflammation. J Clin Invest 2005; 115: 247-257; Cao Y. Opinion: emerging mechanisms of tumour lymphangiogenesis and lymphatic metastasis. Nat Rev Cancer 2005; 5: 735-743]. Lymphangiogenesis, the sprouting of new lymphatic vessels from the pre-existing lymphatic system, may provide a way to facilitate the dissemination of cancer cells to sentinel lymph nodes and further distant organs [Cao Y. Opinion: emerging mechanisms of tumour lymphangiogenesis and lymphatic metastasis. Nat Rev Cancer 2005; 5: 735-743; Gao P, Zhou G Y, Zhang Q H, et al. Lymphangiogenesis in gastric carcinoma correlates with prognosis. J Pathol 2009; 218: 192-200]. VEGF-C and D, the most potent pro-lymphangiogenic factors reported so far, are demonstrated to intensively stimulate lymphangiogenesis, and promote tumor lymphatic metastasis through their receptor VEGFR-3 [Jussila L, Alitalo K. Vascular growth factors and lymphangiogenesis. Physiol Rev 2002; 82: 673-700; Joukov V, Pajusola K, Kaipainen A, et al. A novel vascular endothelial growth factor, VEGF-C, is a ligand for the Flt4 (VEGFR-3) and KDR (VEGFR-2) receptor tyrosine kinases. EMBO J 1996; 15: 290-298; Royston D, Jackson D G. Mechanisms of lymphatic metastasis in human colorectal adenocarcinoma. J Pathol 2009; 217: 608-619]. Other pro-angiogenic factors including VEGF-A, platelet-derived growth factor BB (PDGF-BB), angiopoietin-1, hepatocyte growth factor (HGF) and insulin-like growth factor 1/2 (IGF1/2), have also been reported to stimulate lymphangiogenesis [Kajiya K, Hirakawa S, Ma B, et al. Hepatocyte growth factor promotes lymphatic vessel formation and function. EMBO J 2005; 24: 2885-2895; Tammela T, Saaristo A, Lohela M, et al. Angiopoietin-1 promotes lymphatic sprouting and hyperplasia. Blood 2005; 105: 4642-4648; Bjorndahl M, Cao R, Nissen L J, et al. Insulin-like growth factors 1 and 2 induce lymphangiogenesis in vivo. Proc Natl Acad Sci USA 2005; 102: 15593-15598; Cursiefen C, Chen L, Borges L P, et al. VEGF-A stimulates lymphangiogenesis and hemangiogenesis in inflammatory neovascularization via macrophage recruitment. J Clin Invest 2004; 113: 1040-1050; Cao R, Bjorndahl M A, Religa P, et al. PDGF-BB induces intratumoral lymphangiogenesis and promotes lymphatic metastasis. Cancer Cell 2004; 6: 333-345]. While, only alternatively spliced soluble VEGFR-2 has been reported as an endogenous selective lymphangiogenesis inhibitor so far [Albuquerque R J, Hayashi T, Cho W G, et al. Alternatively spliced vascular endothelial growth factor receptor-2 is an essential endogenous inhibitor of lymphatic vessel growth. Nat Med 2009; 15: 1023-1030].

Interestingly, Nakamura group firstly described that endostatin produced by adenovirus-infection in tumor cells inhibits lymph node metastasis [Fukumoto S, Morifuji M, Katakura Y, et al. Endostatin inhibits lymph node metastasis by a down-regulation of the vascular endothelial growth factor C expression in tumor cells. Clin Exp Metastasis 2005; 22: 31-38]. Similar results were observed by Heljasvaara's group in J4 transgenic mice overexpressing endostatin [Brideau G, Makinen M J, Elamaa H, et al. Endostatin overexpression inhibits lymphangiogenesis and lymph node metastasis in mice. Cancer Res 2007; 67: 11528-11535]. Both of these studies imply that the anti-lymphangiogenic effect of endostatin is due to down-regulation of VEGF-C, either by tumor cells or mast cells in the tumor microenvironment. Since it is well accepted that vascular endothelial cells are the direct target of endostatin, it is unclear whether endostatin can directly affect the lymphatic endothelial cells.

As detailed hereinafter, the inventors demonstrate that endostatin directly inhibits mouse lymphatic endothelial cells (mLECs) and lymphangiogenic vessels via cell surface nucleolin as its receptor on mLECs, but does not affect quiescent adult lymphatic vessels. Our discoveries provide a new method of screening the suitable objects for endostatin therapy to prevent tumor lymphangiogenesis and lymph node metastasis.

SUMMARY OF THE INVENTION

The invention is based upon the discovery that nucleolin is specifically expressed on lymphangiogenic vessels and functions as a receptor for endostatin, thus mediates the inhibition of lymphangiogenesis and tumor lymph node metastasis by endostatin. The nucleolin expressed on the surface of lymphatic endothelial cells can also serve as a new biomarker of lymphangiogenic vessels.

In one aspect, the present invention provides a method of determining the likelihood of lymphatic metastasis in a subject with cancer, comprising the step of determining the presence of cell surface nucleolin on lymphatic vessels in a cancer tissue sample or a tissue sample from lymph node adjacent to the cancer tissue from said subject, wherein the presence of cell surface nucleolin on lymphatic vessels in the sample is indicative of higher likelihood of lymphatic metastasis in said subject.

In another aspect, the present invention provides a method of determining the prognosis of a subject with cancer, comprising the step of determining the presence of cell surface nucleolin on lymphatic vessels in a cancer tissue sample or a tissue sample from lymph node adjacent to the cancer tissue from said subject, wherein the presence of cell surface nucleolin on lymphatic vessels in the sample is indicative of an unfavorable prognosis of said subject.

In another aspect, the present invention provides a method of determining the susceptibility of a cancer in a subject to endostatin therapy, comprising the step of determining the presence of cell surface nucleolin on lymphatic vessels in a cancer tissue sample or a tissue sample from lymph node adjacent to the cancer tissue from said subject, wherein the presence of cell surface nucleolin on lymphatic vessels in the sample is indicative of a higher susceptibility of the cancer to endostatin therapy.

In another aspect, the present invention provides a method of screening a nucleolin-specific lymphangiogenesis inhibitor, comprising the steps of applying an appropriate binding assay to a pool of candidate molecules, thereby obtaining a plurality of nucleolin-specific molecules that specifically interact with cell surface nucleolin; testing each of the plurality of nucleolin-specific molecules for its effectiveness of inhibiting lymphangiogenesis by carrying out an anti-lymphangiogenesis assay; and selecting a nucleolin-specific molecule which is effective in inhibiting lymphangiogenesis as demonstrated by the anti-lymphangiogenesis assay.

In another aspect, the present invention provides a method of treating a cancer subject having or suspected to have lymphatic metastasis, comprising the steps of determining the presence of cell surface nucleolin on lymphatic vessels in a cancer tissue sample or a tissue sample from lymph node adjacent to the cancer tissue from said subject, and administering a nucleolin-specific anti-lymphangiogenic agent to a subject who is determined as positive for the presence of cell surface nucleolin on lymphatic vessels in the sample.

In another aspect, the present invention provides a method of preventing lymphatic metastasis in a cancer subject, comprising the steps of determining the presence of cell surface nucleolin on lymphatic vessels in a cancer tissue sample or a tissue sample from lymph node adjacent to the cancer tissue from said subject, and administering a nucleolin-specific anti-lymphangiogenic agent to a subject who is determined as positive for the presence of cell surface nucleolin on lymphatic vessels in the sample.

In another aspect, the present invention provides a method of preventing or inhibiting the proliferation and/or migration of lymphatic endothelial cells in a cancer subject, comprising the steps of determining the presence of cell surface nucleolin on lymphatic vessels in a cancer tissue sample or a tissue sample from lymph node adjacent to the cancer tissue from said subject, and administering a nucleolin-specific anti-lymphangiogenic agent to a subject who is determined as positive for the presence of cell surface nucleolin on lymphatic vessels in the sample.

In another aspect, the present invention provides a method of selecting an lymphangiogenesis inhibitor having the ability to inhibit lymphatic endothelial proliferation and/or migration when added to proliferating lymphatic endothelial cells in vitro, comprising the steps of performing a suitable assay to identify and obtain a nucleolin-specific molecule that specifically interact with surface nucleolin on lymphatic endothelial cells; testing the nucleolin-specific molecule thus obtained for its effectiveness in inhibiting lymphatic endothelial cell proliferation and/or migration; and selecting a nucleolin-specific molecule which is effective in inhibition of lymphatic endothelial cell proliferation and/or migration.

DETAILED DESCRIPTION OF THE INVENTION

Figure 1:
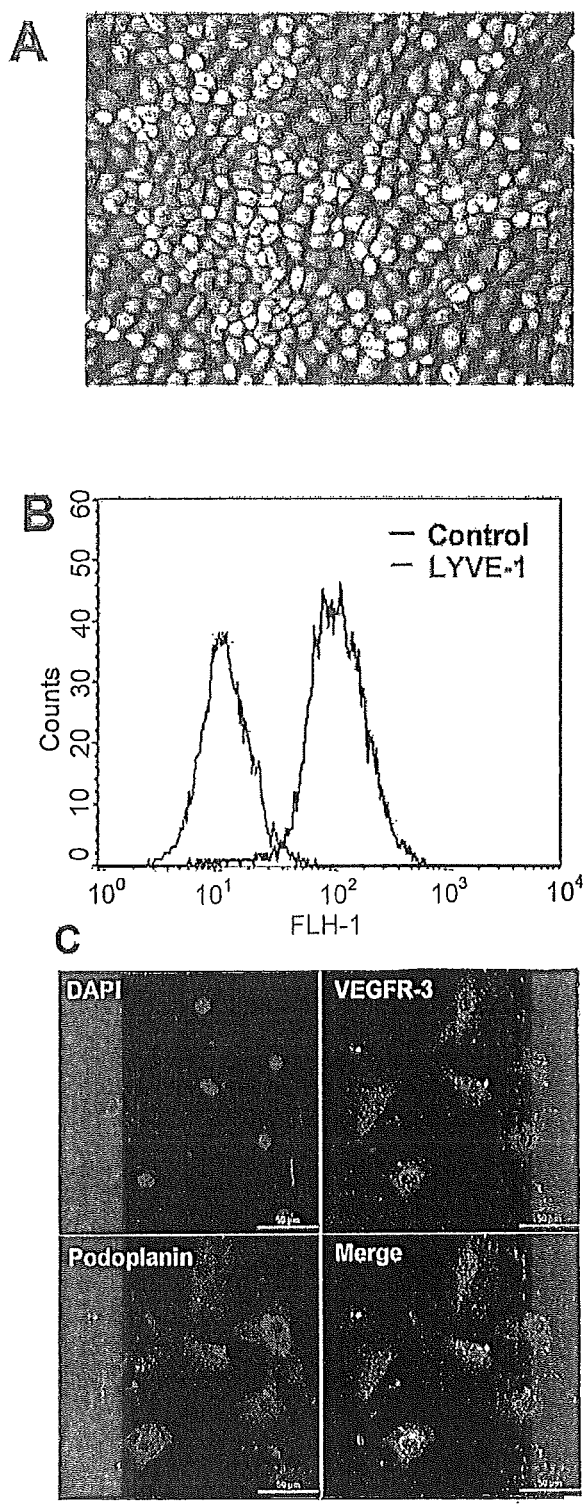
FIG. 1 shows the isolation and characterization of primary mLECs. A. Phase-contrast microscopy of cultured primary mLECs monolayer. ×200. B. FACS analysis of purified mLECs stained with the anti-mouse LYVE-1 antibody. Black: negative control; pink: LYVE-1. C. Immunofluorescence analysis showing the expression of podoplanin and VEGFR-3 on cultured primary mLECs.

Nucleolin is a ubiquitous, nonhistone protein, which was first isolated from nucleolus. It is very interesting that the amount of nucleolin is correlated to cell proliferation, which is regulated by Granzyme A and self-cleaving activity. Nucleolin also undergoes self-cleavage, which is decreased when cells enter a proliferative stage, as well as being cleaved by Granzyme A, an esterase secreted by cytotoxic lymphocytes (Chen et al., J. Biol. Chem., 1991, 266, 7754-7758; Fang and Yeh, Exp. Cell. Res., 1993, 208, 48-53; Pasternack et al., J. Biol. Chem., 1991, 266, 14703-14708). The cleavage and concomitant degradation of the protein provides for post-translational regulation of nucleolin.

As a multifunctional protein, nucleolin exerts a critical and fundamental effect on cell proliferation, including organization of nucleolar chromatin, packaging of pre-RNA, rDNA transcription, and ribosome assembly. These activities are regulated by certain protein kinases such as casein kinase 2 (CK2) and cdc2 which are under strict control of other cell cycle proteins. Moreover, nucleolin also functions as a cell surface receptor, shuttling between cell surface, cytoplasm, and nucleus. As a receptor of many viruses and cytokines, nucleolin triggers the internalization of ligands as soon as these ligands bind to it.

Nucleolin has been described by Orrick et al (1973) as a protein with molecular weight about 100-110 kDa, and mainly existing in the nucleus of the propagating cells. Nucleolin exhibits auto-degradation and shows two degraded bands about 70 and 50 kDa in Western blotting analysis. Nucleolin is highly phosphorylated and methylated, and can be ADP-ribosylated. Because synthesis of the nucleolin is positively correlated with increased rate of cell division, tumor cells and rapidly dividing cells have higher levels of nucleolin content. The sequence of nucleolin was reported earlier in Srivastava, et al., Cloning and sequencing of the human nucleolin cDNA. FEBS Lett. 250 (1), 99-105 (1989).

Nucleolin (also known as P92 and C23) is the most abundant nucleolar phosphoprotein in actively growing cells (Srivastava et al., FEBS Lett., 1989, 250, 99-105; Srivastava et al., J. Biol. Chem., 1990, 265, 14922-14931). It has been described by several groups and shown to participate primarily in ribosome biogenesis (Ghisolfi et al., Mol. Biol. Rep., 1990, 14, 113-114; Sipos and Olson, Biochem. Biophys. Res. Commun., 1991, 177, 673-678) and transport of ribosomal components (Schmidt-Zachmann et al., Cell, 1993, 74, 493-504). Nucleolin contributes to ribosome biosynthesis by transiently binding to the pre-ribosomes in the nucleolus via a ribonucleoprotein consensus sequence (Bugler et al., J. Biol. Chem., 1987, 262, 10922-10925; Ghisolfi-Nieto et al., J. Mol. Biol., 1996, 260, 34-53; Sapp et al., Eur. J. Biochem., 1989, 179, 541-548). Here, nucleolin can represent up to 5% of the total nucleolar protein (Lapeyre et al., Proc. Natl. Acad. Sci. U.S.A., 1987, 84, 1472-1476; Sapp et al., Eur. J. Biochem., 1989, 179, 541-548). However, it has also been shown to be involved in cytokinesis, nucleogenesis, cell proliferation and growth, transcriptional repression, replication, signal transduction and chromatin decondensation reviewed in (Tuteja and Tuteja, Crit. Rev. Biochem. Mol. Biol., 1998, 33, 407-436).

The multifunctionality of this protein arises from the presence of distinct structural and functional domains within the protein (Creancier et al., Mol. Biol. Cell., 1993, 4, 1239-1250; Sapp et al., Eur. J. Biochem., 1989, 179, 541-548). Three domains have been described within the nucleolin protein, the N-terminal domain, the central domain and the C-terminal domain. Contained in the N-terminal domain are sequences that show homology with the high-mobility group (HMG) and are responsible for interactions with chromatin (Erard et al., Eur. J. Biochem., 1988, 175, 525-530). The central domain contains four RNA recognition motifs and binds specifically with the short stem loop of the 18S and 28S ribosomal RNA (Bugler et al., J. Biol. Chem., 1987, 262, 10922-10925) while the C-terminal domain contains regions that are capable of unstacking bases in RNA (Ghisolfi et al., Mol. Biol. Rep., 1990, 14, 113-114; Ghisolfi-Nieto et al., J. Mol. Biol., 1996, 260, 34-53). Nucleolin contains a bipartite nuclear localization signal, spanning both the N-terminal and central regions of the protein, which facilitates transport into the nucleus where nucleolin accumulates due to interactions with other proteins (Schmidt-Zachmann and Nigg, J. Cell Sci., 1993, 105, 799-806).

The domain structure of nucleolin has led the protein to be classified as an Ag-NOR protein (Active ribosomal gene located in the Nucleolar Organizer Region) otherwise known as markers of active ribosomal genes (Roussel et al., Exp. Cell. Res., 1992, 203, 259-269). It has been shown that transcription of ribosomal genes requires the presence of Ag-NOR proteins and the expression of Ag-NOR proteins has been associated with the prediction of tumor growth rate in cancers.

Nucleolin has also been purified as a matrix attachment region (MAR) binding protein from human erythroleukemia cells. In these studies, nucleolin was shown to participate in the anchoring of chromatin loops to the nuclear matrix (Dickinson and Kohwi-Shigematsu, Mol. Cell. Biol., 1995, 15, 456-465).

Nucleolin is highly phosphorylated and has been shown to be a substrate for casein kinase II (Csermely et al., J. Biol. Chem., 1993, 268, 9747-9752; Schneider and Issinger, Biochem. Biophys. Res. Commun., 1988, 156, 1390-1397), Protein kinase C-.xi. (Zhou et al., J. Biol. Chem., 1997, 272, 31130-31137), and Cdc2 (Belenguer et al., Mol, Cell. Biol., 1990, 10, 3607-3618). Furthermore, the phosphorylation of nucleolin has been shown to regulate the subcellular localization of the protein.

Nucleolin also undergoes self-cleavage, which is decreased when cells enter a proliferative stage, as well as being cleaved by Granzyme A, an esterase secreted by cytotoxic lymphocytes (Chen et al., J. Biol. Chem., 1991, 266, 7754-7758; Fang and Yeh, Exp. Cell. Res., 1993, 208, 48-53; Pasternack et al., J. Biol. Chem., 1991, 266, 14703-14708). The cleavage and concomitant degradation of the protein provides for post-translational regulation of nucleolin.

Anti-nucleolin antibodies have been found in the sera of patients with systemic connective tissue diseases including systemic lupus erythromatosus (SLE) (Minota et al., J. Immunol., 1990, 144, 1263-1269; Minota et al., J. Immunol., 1991, 146, 2249-2252) and scleroderma-like chronic graft vs. host disease (Bell et al., Br. J. Dermatol., 1996, 134, 848-854). The pharmacological modulation of nucleolin expression may therefore be an appropriate point of therapeutic intervention in pathological conditions.

It is believed that expression level of nucleolin correlates with cell proliferation rate. Nucleolin levels are highest in tumors and moderate in other rapidly dividing cells. It can be used in studies of different cancer cell lines as useful marker for cell proliferation. Since nucleolin plays a vital role in tumor cell proliferation, the present invention provides a strategy of inhibition of nucleolin expression to suppress the growth rate of tumor cells.

Endostatin is a 20 kDa C-terminal globular domain of the collagen-like protein, collagen XVIII. It was originally isolated from the supernatant of a cultured murine hemangioendothelioma cell line for its ability to inhibit the proliferation of capillary endothelial cells. In animal tests, tumor dormancy was induced following repeated cycles of endostatin treatment without any drug resistance. Moreover, low toxicity of endostatin was observed in both animal tests and clinical trials. Endostatin exhibits potent activities in inhibiting endothelial cell proliferation, migration, adhesion, survival, and in inducing cell apoptosis.

Our previous discovery disclosed that cell surface nucleolin functions as a receptor for endostatin [Shi H, Huang Y, Zhou H, et al. Nucleolin is a receptor that mediates antiangiogenic and antitumor activity of endostatin. Blood 2007; 110: 2899-2906]. It is found that nucleolin specifically locates on angiogenic blood vessels and mediates the antiangiogenic and anti-tumor activities of endostatin.

In the present invention, it is further surprisingly discovered that nucleolin is selectively expressed on the surface of active lymphatic endothelial cells in lymphangiogenic vessels and thus can serve as a biomarker of lymphangiogenic vessels.

Lymphangiogenesis, the sprouting of new lymphatic vessels from the pre-existing lymphatic system, may provide a way to facilitate the dissemination of cancer cells to sentinel lymph nodes and further distant organs [Cao Y. Opinion: emerging mechanisms of tumour lymphangiogenesis and lymphatic metastasis. Nat Rev Cancer 2005; 5: 735-743; Gao P, Zhou G Y, Zhang Q H, et al. Lymphangiogenesis in gastric carcinoma correlates with prognosis. J Pathol 2009; 218: 192-200].

The present invention thus provides a method of determining the likelihood of lymphatic metastasis in a subject with cancer, comprising the step of determining the presence of cell surface nucleolin on lymphatic vessels in a cancer tissue sample or a tissue sample from lymph node adjacent to the cancer tissue from said subject, wherein the presence of cell surface nucleolin on lymphatic vessels in the sample is indicative of higher likelihood of lymphatic metastasis in said subject.

The present invention also provides a method of determining the prognosis of a subject with cancer, comprising the step of determining the presence of cell surface nucleolin on lymphatic vessels in a cancer tissue sample or a tissue sample from lymph node adjacent to the cancer tissue from said subject, wherein the presence of cell surface nucleolin on lymphatic vessels in the sample is indicative of an unfavorable prognosis of said subject.

The term "cell surface nucleolin" as used herein refers to nucleolin selectively expressed on the surface of active lymphatic endothelial cells in lymphangiogenic vessels.

The term "lymph node adjacent to the cancer tissue" as used herein refers to the hypothetical first lymph node or group of lymph nodes draining a cancer when cancerous dissemination occurs. The term "lymph node adjacent to the cancer tissue" includes the sentinel lymph nodes which are the target organs primarily reached by metastasizing cancer cells from the tumor.

In the present invention, it is also demonstrated that cell surface nucleolin on lymphatic vessels functions as a receptor for endostatin, and mediates the inhibition of lymphangiogenesis and tumor lymph node metastasis by endostatin.

Accordingly, the present invention further provides a method of determining the susceptibility of a cancer in a subject to endostatin therapy, comprising the step of determining the presence of cell surface nucleolin on lymphatic vessels in a cancer tissue sample or a tissue sample from lymph node adjacent to the cancer tissue from said subject, wherein the presence of cell surface nucleolin on lymphatic vessels in the sample is indicative of a higher susceptibility of the cancer to endostatin therapy. Finding this particular group of patients is extremely beneficial to the effectiveness of endostatin cancer therapy, since patients with high expression of cell surface nucleolin on lymphatic vessels are ideal for the administration of endostatin in order to inhibit their lymphatic metastasis.

The present invention also provides a method of screening a nucleolin-specific lymphangiogenesis inhibitor, comprising the steps of applying an appropriate binding assay to a pool of candidate molecules, thereby obtaining a plurality of nucleolin-specific molecules that specifically interact with cell surface nucleolin; testing each of the plurality of nucleolin-specific molecules for its effectiveness of inhibiting lymphangiogenesis by carrying out an anti-lymphangiogenesis assay; and selecting a nucleolin-specific molecule which is effective in inhibiting lymphangiogenesis as demonstrated by the anti-lymphangiogenesis assay.

As used herein, the term "nucleolin-specific" refers to the ability of nucleolin binding to a lymphangiogenesis inhibitor, and mediates its lymphangiogenesis inhibitory activity.

As used herein, an "appropriate binding assay" for selecting nucleolin-specific molecules includes HPLC, immunoprecipitation, fluorescent-binding assay, capillary electrophoresis, and so forth.

As used herein, an "anti-lymphangiogenesis assay" is an experiment where a pool of candidate molecules are screened in order to discover the effectiveness of the candidate molecules in inhibiting lymphangiogenesis. In order to discover whether a molecule has anti-lymphangiogenesis property, various methods can be applied to carry out the present invention. For example, proteins and peptides derived from these and other sources, including manual or automated protein synthesis, may be quickly and easily tested for lymphatic endothelial cells proliferation/migration inhibiting activity using a biological activity assay such as the mLECs tubule formation assay and the modified Boyden chamber assay as used in the Examples.

In the present invention, it is also demonstrated that that endostatin significantly inhibits tumor lymphangiogenesis, in vivo, which is mediated by its cell surface receptor nucleolin.

Accordingly, the present invention further provides a method of treating a cancer subject having or suspected to have lymphatic metastasis, comprising the steps of determining the presence of cell surface nucleolin on lymphatic vessels in a cancer tissue sample or a tissue sample from lymph node adjacent to the cancer tissue from said subject, and administering a nucleolin-specific anti-lymphangiogenic agent to a subject who is determined as positive for the presence of cell surface nucleolin on lymphatic vessels in the sample.

The present invention also provides a method of preventing lymphatic metastasis in a cancer subject, comprising the steps of determining the presence of cell surface nucleolin on lymphatic vessels in a cancer tissue sample or a tissue sample from lymph node adjacent to the cancer tissue from said subject, and administering a nucleolin-specific anti-lymphangiogenic agent to a subject who is determined as positive for the presence of cell surface nucleolin on lymphatic vessels in the sample.

The present invention further provides a method of preventing or inhibiting the proliferation and/or migration of lymphatic endothelial cells in a cancer subject, comprising the steps of determining the presence of cell surface nucleolin on lymphatic vessels in a cancer tissue sample or a tissue sample from lymph node adjacent to the cancer tissue from said subject, and administering a nucleolin-specific anti-lymphangiogenic agent to a subject who is determined as positive for the presence of cell surface nucleolin on lymphatic vessels in the sample.

As used herein, the expression "positive for the presence of cell surface nucleolin on lymphatic vessels" refers to a tissue sample which has nucleolin expression on the surface of lymphatic endothelial cells, and the cell surface nucleolin co-localizes with lymphatic vessels, e.g., as revealed by an immunohistochemistry assay.

As used herein, the term "nucleolin-specific anti-lymphangiogenic agent" refers to any agent that can selectively bind to cell surface nucleolin on lymphatic vessels and inhibit the proliferation/migration of lymphatic endothelial cells.

In one embodiment, the nucleolin-specific anti-lymphangiogenic agent is endostatin. As used herein, the term "endostatin" refers to a protein that is preferably 18 kDa to 21 kDa in size as determined by non-reduced and reduced gel electrophoresis, respectively. The term endostatin also includes precursor forms of the 18 kDa to 20 kDa protein. The term endostatin also includes fragments of the 18 kDa to 20 kDa protein and modified proteins and peptides that have a substantially similar amino acid sequence, and which are capable of inhibiting proliferation of endothelial cells. For example, silent substitutions of amino acids, wherein the replacement of an amino acid with a structurally or chemically similar amino acid does not significantly alter the structure, conformation or activity of the protein, is well known in the art. Such silent substitutions are intended to fall within the scope of the appended claims.

In a preferable embodiment, the nucleolin-specific anti-lymphangiogenic agent is a conjugate comprising endostatin. For example, the conjugate may be endostatin covalently linked to a modifier capable of prolonging its half-life and/or enhancing its biological activity.

There are many methods known in the art to prolong the half-life and/or enhance the biological activity of a therapeutic agent. For example, US 2010-0285103 A1 (the entire content of which is incorporated herein by reference) discloses a conjugate comprising endostatin covalently linked to PEG molecule, in which the PEG molecule is covalently linked to the N-terminal a amino group of endostatin. The PEG molecule that may be used to modify endostatin may have a molecular weight from 5-100 kD, and preferably from 20-40 kD.

In another embodiment, the conjugate may comprise endostatin linked to a cytotoxic agent, such as a chemokine, e.g., a Tumor Necrosis Factor-alpha, etc. When such a conjugate is administered to the cancer subject, the endostatin will direct the cytotoxic agent to the cell surface nucleolin on lymphatic vessels in or adjacent to cancer tissue, and thus bring the cytotoxic agent such as Tumor Necrosis Factor-alpha to act upon the active lymphatic endothelial cells, and killing the cell growth.

In another embodiment, the nucleolin-specific anti-lymphangiogenic agent comprises a nucleolin-specific molecule selected by the method of the present invention for screening a nucleolin-specific lymphangiogenesis inhibitor.

In yet another embodiment, the nucleolin-specific anti-lymphangiogenic agent comprises an anti-nucleolin antibody. Accordingly, the present invention provides a method of treating a cancer subject having or suspected to have lymphatic metastasis, a method of preventing lymphatic metastasis in a cancer subject, or a method of preventing or inhibiting the proliferation and/or migration of lymphatic endothelial cells in a cancer subject, comprising the steps of determining the presence of cell surface nucleolin on lymphatic vessels in a cancer tissue sample or a tissue sample from lymph node adjacent to the cancer tissue from said subject, and administering an anti-nucleolin antibody to a subject who is determined as positive for the presence of cell surface nucleolin on lymphatic vessels in the sample.

The anti-nucleolin antibody may be linked to a cytotoxic agent, such as a chemokine, e.g., a Tumor Necrosis Factor-alpha, etc. When such a combination antibody is administered to the cancer subject, the anti-nucleolin antibody will direct the cytotoxic agent to the cell surface nucleolin on lymphatic vessels in or adjacent to cancer tissue, and thus bring the cytotoxic agent such as Tumor Necrosis Factor-alpha to act upon the active lymphatic endothelial cells, and killing the cell growth.

As used herein, the term "subject" refers to any animal, such as a mammal, including but not limited to a human, a non-human primate, a rodent, a pig, a rabbit, and the like, which is to receive a particular treatment, or undergoing a particular procedure such as screening for the level of presence of a particular molecule. In a particular embodiment, the subject is a human.

Detection of the protein molecule of nucleolin can be performed using techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In a preferable embodiment of the detection methods used in the present invention, the step of determining the presence of cell surface nucleolin on lymphatic vessels is performed by carrying out an immunoassay with an antibody that specifically binds to nucleolin. Antibodies specific for nucleolin are made according to techniques and protocols well known in the art. The antibodies may be either polyclonal or monoclonal. The antibody also covers an antigen binding fragment of a monoclonal antibody specific for nucleolin.

As used herein, the term "sample" refers to a tissue specimen removed from the cancer lesion from a cancer subject, for example, by surgical resection or biopsy.

The present invention also provides a method of selecting an lymphangiogenesis inhibitor having the ability to inhibit lymphatic endothelial proliferation and/or migration when added to proliferating lymphatic endothelial cells in vitro, comprising the steps of performing a suitable assay to identify and obtain a nucleolin-specific molecule that specifically interact with surface nucleolin on lymphatic endothelial cells; testing the nucleolin-specific molecule thus obtained for its effectiveness in inhibiting lymphatic endothelial cell proliferation and/or migration; and selecting a nucleolin-specific molecule which is effective in inhibition of lymphatic endothelial cell proliferation and/or migration.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Isolation and Culture of Primary mLECs

MLECs were isolated from the hyperplastic lymphatic vessels induced by incomplete Freund's adjuvant as described previously [Mancardi S, Stanta G, Dusetti N, et al. Lymphatic endothelial tumors induced by intraperitoneal injection of incomplete Freund's adjuvant. Exp Cell Res 1999; 246: 368-375]. In Brief, BALB/c mice (female, 4-6 weeks) were intraperitoneally injected twice (day 0 and day 14) with 200 µL incomplete Freund's adjuvant (1:1 mixed with PBS). Hyperplastic lymphatic vessels were isolated from diaphragm and liver on day 21, and digested with 1 mg/mL collagenase solution (collagenase I/collagenase II=1:1) at 37° C. for 20 min. Single-cell suspension was collected and further purified using a goat anti-rabbit LYVE-1 antibody with magnetic cell sorting (MACS) microbeads (Miltenyi Biotec GmbH). Cells were seeded in plasticware pre-coated with 1% gelatin in PBS (37° C., 2 h) and cultured in ECM supplemented with ECGS and 10% fetal bovine serum, 100 µg/mL heparin, 100 µg/mL streptomycin and penicillin. The confluent primary mLECs showed typical cobblestone-like morphology (FIG. 1A), and were characterized as LYVE-1 positive by flow cytometry and podoplanin and VEGFR-3 positive by immunocytochemisty (FIGS. 1B and C). These results demonstrate that the isolated primary mLECs remain characteristic of lymphatic endothelial cells, and express lymphatic lineage markers in vitro.

Example 2

Nucleolin is Expressed on the Cell Surface of Lymphangiogenic Endothelial Cells In Vitro Cultured mLECs were subjected to standard protocol of immunofluorescence and flow cytometry to detect the expression of cell surface nucleolin, in which rabbit polyclonal antibody against nucleolin was used.

Immunofluorescent images were obtained using Nikon microscope A1R/A1 (Nikon, Japan) or Olympus microscope (Olympus, Japan) and analyzed by NIS-Elements AR 3.0. FACS Calibur flow cytometry system (Becton Dickinson, San Jose, Calif.) was also used to detect and analyze cell surface nucleolin.

Figure 2:
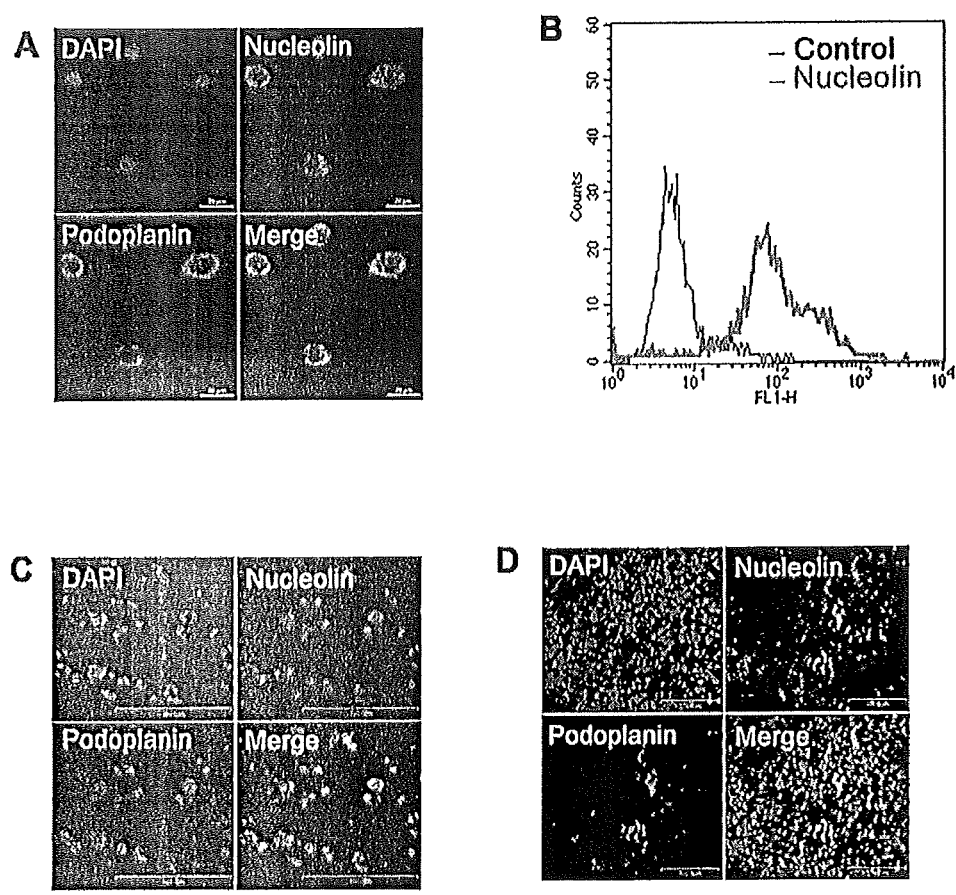
FIG. 2 shows the expression of nucleolin on the cell surface of lymphangiogenic endothelial cells as demonstrated both in vitro and in vivo. A. Detection of cell surface nucleolin on isolated mLECs by immunofluorescence. B. Flow cytometric detection of cell surface nucleolin on isolated mLECs. C. Detection of cell surface nucleolin on newly formed lymphatic vessels in Matrigel plug assay. Matrigel containing VEGF-C (500 ng/mL) was injected subcutaneously near the abdominal midline of BALB/c mouse. After 8 days, Matrigel plug was dissected and immunofluorescent detection of podoplanin and nucleolin was performed. D. Expression of cell surface nucleolin on lymphatic vessels in primary human gastric cancer. Lymphatic vessels were immunostained for podoplanin. Merge indicates expression of nucleolin on lymphatic vessels in tumor tissue. Blue: DAPI; green: nucleolin; red: podoplanin. Immunofluorescent images were visualized using confocal microscope (Olympus). Scale bar, 20 μm for (A), 100 μm for (C and D).

As expected, nucleolin was detected on the cell surface of mLECs (FIGS. 2A and B).

Example 3

Nucleolin is Expressed on the Cell Surface of Lymphangiogenic Endothelial Cells In Vivo In Matrigel plug assay, BALB/c (female, 5 weeks old, 5 per group) mice were subcutaneously injected with 0.5 mL Matrigel (9-10 mg/mL, Becton-Dickinson Labware, MA). After 8 days, Matrigels were dissected and fixed in 4% paraformaldehyde for the immunohistochemical analysis. Primary human gastric carcinoma tissue was also dissected and fixed in 4% paraformaldehyde for the immunohistochemical analysis. Standard protocol of immunohistochemistry was employed to detect cell surface nucleolin expression in both Matrigel plugs and human tissue samples, in which podoplanin served as a marker of mLECs.

Obviously, nucleolin was highly expressed on the newly formed lymphatic vessels in Matrigel plug as shown by the co-localization of nucleolin and podoplanin (FIG. 2C). Consistent results were obtained from tumor associated lymphatic vessels in primary human gastric carcinoma tissue (FIG. 2D). These observations demonstrate that nucleolin is indeed expressed on the cell surface of lymphangiogenic endothelial cells in vivo.

Example 4

Endostatin can Directly Bind to Cell Surface of mLECs

Figure 3:
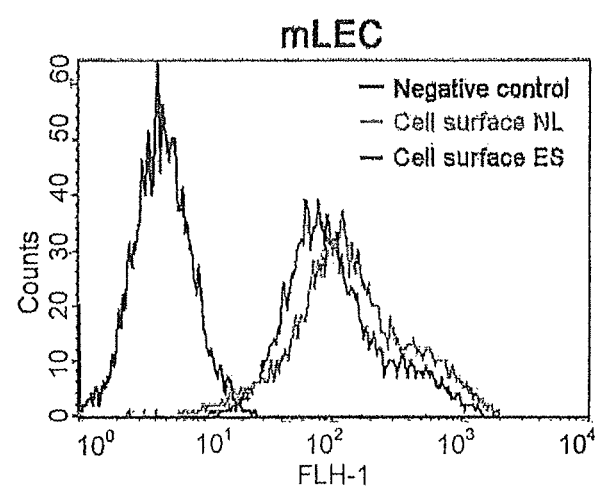
FIG. 3 shows the direct binding of endostatin to cell surface of mLECs. Cultured mLECs were incubated with endostatin (5 μg/mL) for 30 min. Cells were washed three times with cold PBS, harvested with 0.5 mM EDTA and applied to flow cytometry. Cell surface endostatin was analyzed using anti-endostatin antibody. Expression level of nucleolins on untreated mLECs was also detected.

Cultured mLECs were incubated with endostatin (5 µg/mL) for 30 min. Cells were washed three times with cold PBS, harvested with 0.5 mM EDTA and applied to flow cytometry. Cell surface endostatin was analyzed using rabbit polyclonal antibody against endostatin. Expression level of nucleolins on untreated mLECs was also detected. NL: nucleolin; ES: endostatin (FIG. 3).

Flow cytometric result revealed that endostatin can directly bind to cell surface of mLECs, which is essential for the direct anti-lymphatic endothelial activity of endostatin.

Example 5

Endostatin Shows Anti-Lymphangiogenic Activity In Vitro

Cell migration was assessed using a modified Boyden chamber (8 µm pores, Costar) [Shi H, Huang Y, Zhou H, et al. Nucleolin is a receptor that mediates antiangiogenic and antitumor activity of endostatin. Blood 2007; 110: 2899-2906]. MLECs were pretreated with endostatin at indicated concentrations for 30 min. Subsequently, mLECs (2×104 cells in 100 µl) were seeded in 1% FBS-containing ECM in the upper chambers. In the presence or absence of 100 ng/mL of VEGF-C, endostatin at indicated concentrations was added in both the upper chamber and lower chamber. After incubation for 6 h at 37° C., the migrated cells were quantified by counting in eight high-power (400×) fields under the Olympus IX71 optical microscope. Each experiment was analyzed in triplicate.

Tubule formation assay was conducted as previously described [Garmy-Susini B, Makale M, Fuster M, et al. Methods to study lymphatic vessel integrins. Methods Enzymol 2007; 426: 415-438] and performed in parallel with that of migration assay. Tubule structures were imaged by the Olympus IX71 optical microscope and quantified by measuring length of cords in eight randomly imaged fields using NIH Image J software. One cord was defined as the length between two intersecting points [Iruela-Arispe M L, Bornstein P, Sage H. Thrombospondin exerts an antiangiogenic effect on cord formation by endothelial cells in vitro. Proc Natl Acad Sci USA 1991; 88: 5026-5030]. Experiments were performed in triplicate and repeated twice.

Figure 4:
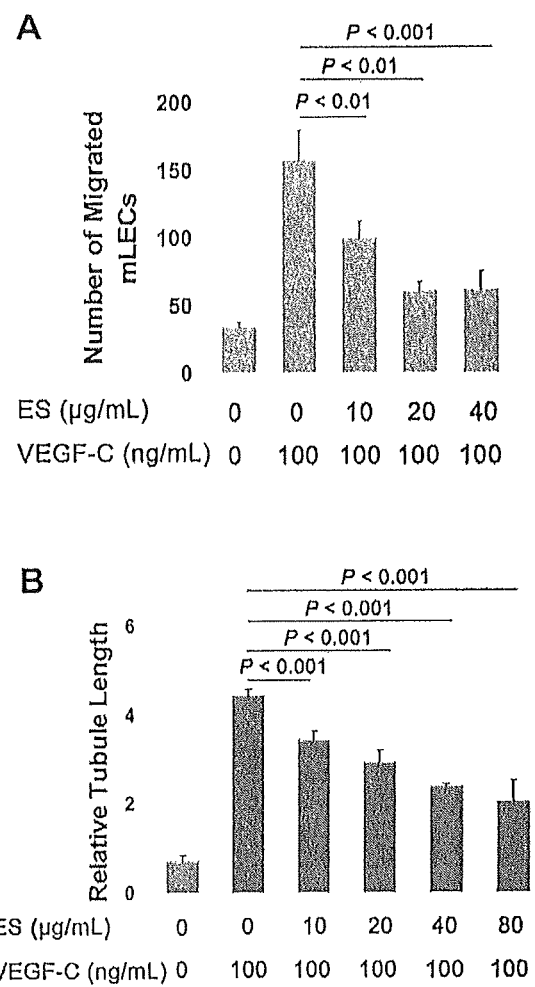
FIG. 4 shows the anti-lymphangiogenic activity of endostatin in vitro. A. Effects of endostatin on the migration of isolated mLECs were determined using modified Boyden chamber assay. Endostatin pretreated primary mLECs were seeded to each upper well with or without VEGF-C (100 ng/mL)-stimulation. Endostatin at indicated concentrations (10, 20, 40 μg/mL) was added into VEGF-C-stimulated medium. MLECs were allowed to migrate for 6 h. B. Effects of endostatin on the tubule formation of isolated mLECs. Endostatin pretreated primary mLECs were cultured on Matrigel-coated 24-wells with or without VEGF-C (100 ng/mL)-stimulation. Endostatin at indicated concentrations (10, 20, 40, 80 μg/mL) was added into VEGF-C-stimulated medium. Cells were incubated for 8 h.

Endostatin directly inhibited the VEGF-C-induced migration of mLECs in a dose-dependent manner in a modified Boyden chamber assay (FIG. 4A). Similarly, endostatin dramatically inhibited the tubule-like structure formation of mLECs in a dose-dependent manner, as quantified by measuring length of cord formed by mLECs (FIG. 4B).

Example 6

Cell Surface Nucleolin Mediates the Anti-Migratory Function of Endostatin on mLECs In Vitro In the modified Boyden chamber assay, mLECs were pretreated with or without endostatin (20 µg/mL) for 30 min. In the presence or absence of endostatin, PBS (control), control IgG (40 µg/mL), or anti-nucleolin antibody (40 µg/mL) was added into the culture medium, respectively. MLECs were allowed to migrate for 6 h before quantification of migrated cells.

In the presence or absence of endostatin (20 µg/mL), migration assay was performed with mLECs transfected with N.C. or siRNA-nucleolin. The sequence of double-strand siRNA for nucleolin is: 5'-agaaauugauggacgaucugtt-3'. Negative control scrambled siRNA was purchased from GenePharma (Shanghai, China). The siRNA were transfected with lipofectamine 2000 reagent (Invitrogen, Frederick, Md.) according to manufacturer's specifications. Knockdown efficiency was detected by western blotting 72 h after transfection. Cells were allowed to migrate for 6 h. Number of migrated cells was quantified.

Figure 5:
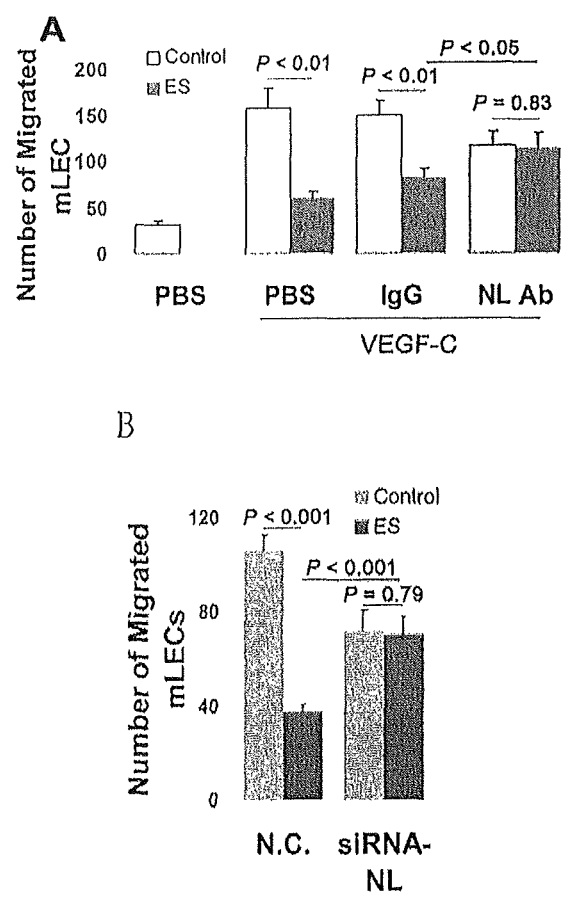
FIG. 5 shows that cell surface nucleolin mediates the anti-migratory function of endostatin on mLECs in vitro. A. In the modified Boyden chamber assay, mLECs were pretreated with or without endostatin (20 μg/mL) for 30 min. In the presence or absence of endostatin, PBS (control), control IgG (40 μg/mL), or anti-nucleolin antibody (40 μg/mL) was added into the culture medium, respectively. MLECs were allowed to migrate for 6 h. B. In the presence or absence of endostatin (20 μg/mL), migration assay was performed with mLECs transfected with N.C. or siRNA-nucleolin. Cells were allowed to migrate for 6 h. Number of migrated cells was quantified and shown.

Anti-nucleolin antibody abrogated the endostatin-induced inhibition of mLECs migration, whereas control IgG could not (FIG. 5A). Similar result was obtained on mLECs transfected with siRNA specific for nucleolin (FIG. 5B). These migration assay showed that the activities of endostatin can be abolished by either anti-nucleolin antibody or nucleolin knocked down. These data suggest that cell surface nucleolin on mLECs mediates the anti-migratory function of endostatin on mLECs in vitro.

Example 7

Cell Surface Nucleolin Mediates the Inhibitory Effect of Endostatin on Tubule Formation of mLECs In Vitro In the tubule formation assay, mLECs were pretreated with or without endostatin (40 µg/mL) for 30 min, and then cultured on Matrigel-coated 24-wells in the presence or absence of endostatin. PBS (control), control IgG (80 µg/mL), or anti-nucleolin antibody (80 µg/m) with or without endostatin (40 µg/mL) was added into the culture medium, respectively. Cells were incubated for 8 h.

Figure 6:
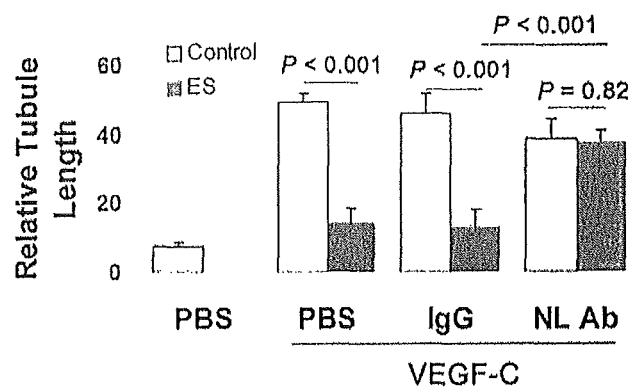
FIG. 6 shows that cell surface nucleolin mediates the inhibitory effect of endostatin on tubule formation of mLECs in vitro. In the tubule formation assay, mLECs were pretreated with or without endostatin (40 μg/mL) for 30 min, and then cultured on Matrigel-coated 24-wells in the presence or absence of endostatin. PBS (control), control IgG (80 μg/mL), or anti-nucleolin antibody (80 μg/m) was added into the culture medium, respectively. Cells were incubated for 8 h.

Anti-nucleolin antibody abrogated the endostatin-induced inhibition of mLECs tubule formation, whereas control IgG could not (FIG. 6), which is consistent with the mLECs migration assay Example 8

Cell Surface Nucleolin Mediates Anti-Lymphangiogenic Function of Endostatin in Vivo Lymphangiogenesis in vivo was evaluated by Matrigel plug assay as previously described [Hirakawa S, Hong Y K, Harvey N, et al. Identification of vascular lineage-specific genes by transcriptional profiling of isolated blood vascular and lymphatic endothelial cells. Am J Pathol 2003; 162: 575-586]. BALB/c mice (female, 5 weeks old, 5 per group) were subcutaneously injected with 0.5 mL Matrigel (9-10 mg/mL, Becton-Dickinson Labware, M A) containing PBS (control) alone or VEGF-C (500 ng/mL), in the presence of PBS, control IgG (80 µg/mL), anti-nucleolin antibody (80 µg/mL), with or without endostatin (40 µg/mL).

Figure 7:
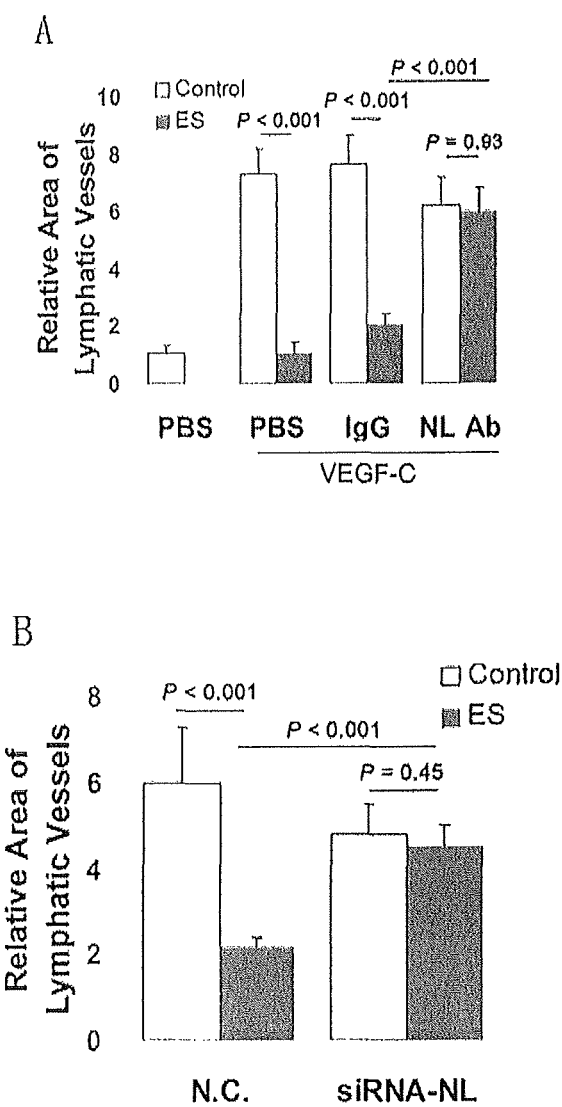
FIG. 7 shows that cell surface nucleolin mediates anti-lymphangiogenic function of endostatin in vivo. A. Density of lymphatic vessels in Matrigel plug assay. Quantification of density of lymphatic vessels from all plugs using Nikon image software (NIS-Elements AR 3.0). Eight independent fields in different sections were assessed. B. The effect of endostatin (40 μg/mL) on lymphangiogenesis in Matrigel plug containing Lentivirus delivered nucleolin siRNA or not were quantified. After 8 days, Quantification of density of lymphatic vessels from all plugs using Nikon image software (NIS-Elements AR 3.0).

Immunohistochemistry analysis of dissected Matrigel plug was performed after 8 days of inoculation in mouse. Plugs containing VEGF-C showed extensive lymphatic vessels with evidently enlarged morphology, whereas plugs supplemented with endostatin or endostatin in combination with control IgG had markedly reduced lymphatic vessel density. In addition, migrated LECs in plugs were discontinuous and did not form intact vessels. However, Matrigels with anti-nucleolin antibody plus endostatin showed pronounced lymphatic vessel formation, and the migrated LECs formed intact vessels with tubule-like structure. Both the lymphatic vessel density and lymphatic structure of this group are similar to that in plugs with anti-nucleolin antibody alone (FIG. 7A).

In another Matrigel plug assay with lentivirus delivered nucleolin siRNA, 0.5 mL Matrigel containing 500 ng/ml of VEGF-C, 5×106 TU of lentivirus delivered nucleolin siRNA or negative control (GenePharma, Shanghai), and endostatin (40 µg/mL) was injected subcutaneously into BALB/c (female, 5 weeks old, 5 per group) mice. 8 days after implantation, Matrigels were dissected and fixed in 4% paraformaldehyde for the immunohistochemical analysis. The evaluation of lymphatic vessel density was assessed in at least six independent fields in different sections. It shows that when cell surface nucleolin was knocked down, the inhibition of endostatin on lymphatic vessels was lost (FIG. 7B).

These results demonstrate that endostatin inhibits lymphangiogenesis through its cell surface receptor nucleolin in vivo.

Example 9

Endostatin Inhibits B16/F10 Melanoma Tumor Growth

B16/F10 melanoma cells (5×106 cells in 100 μL PBS) were inoculated in the subcutaneous space near the axillary lymph node of C57BL/6 mouse (6-8 weeks old). After 3 days, PBS, endostatin (2 mg/kg), control rabbit IgG (2 mg/kg), endostatin plus control rabbit IgG, the rabbit anti-nucleolin antibody (2 mg/kg), or endostatin plus the rabbit anti-nucleolin antibody were administrated intraperitoneally into the mice (5 mice/group) every other day, respectively. There were 6 injections in total. Tumor volume was calculated by using the standard formula: a×b2×0.52 where a is the longest diameter and b is the shortest diameter.

Figure 8:
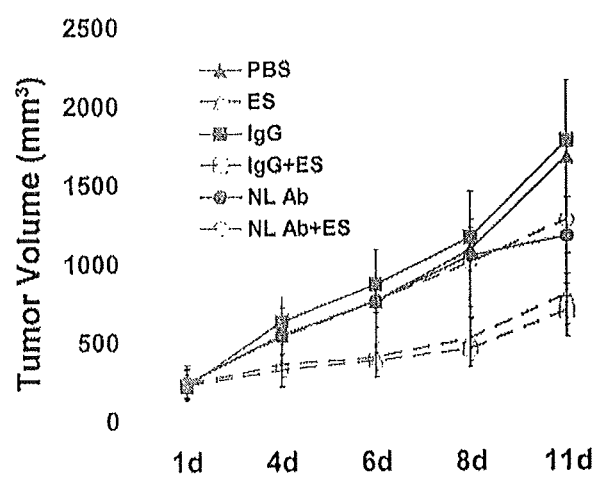
FIG. 8 shows the inhibitory effect of endostatin on B16/F10 melanoma tumor growth. The effects of endostatin and anti-nucleolin antibody on tumor growth in B16/F10 melanoma model are shown. B16/F10 melanoma plug was implanted subcutaneously near to the axillary lymph nodes of C57 mice. Mice were intraperitoneally administrated of PBS, control IgG (2 mg/kg), or anti-nucleolin antibody (2 mg/kg) respectively, with or without endostatin (2 mg/kg) for 11 days. The tumor growth was measured at indicated times after first administration. Mice were intraperitoneally administrated of PBS, control IgG (2 mg/kg), or anti-nucleolin antibody (2 mg/kg) respectively, with or without endostatin (2 mg/kg).

Administration of endostatin efficiently inhibited primary tumor growth as measured by tumor volume (FIG. 8).

Example 10

Endostatin Inhibits Tumor Lymphangiogenesis Via Cell Surface Nucleolin

Inhibitory effect of endostatin on tumor lymphangiogenesis was tested in both subcutaneous B16/F10 melanoma and orthotopic MDA-MB-231 breast cancer models.

Subcutaneous B16/F10 melanoma model were performed as described in Example 9. After 6 injections, tumors were dissected and photographed. 4-6 axillary and inguinal lymph nodes were dissected from each mouse and photographed. Harvested tumors and lymph nodes were fixed in formalin for paraffin embedding. In orthotopic breast cancer models, MDA-MB-231 cells (4×106, in 120 μL Matrigel solution) were inoculated into the mammary fat pad of nude mice (female, 6-8 weeks old). Nine days after inoculation, the mice were randomly divided into 6 groups (5 mice per group). PBS, endostatin (2 mg/kg), control rabbit IgG (2 mg/kg), endostatin plus control rabbit IgG (2 mg/kg), or endostatin plus the rabbit anti-nucleolin antibody were administrated intraperitoneally into the mice every other day, respectively. Three weeks after the first administration, primary tumors, inguinal sentinel lymph nodes, and livers were dissected, fixed in 10% formalin and applied to immunohistochemical analysis.

Figure 9:
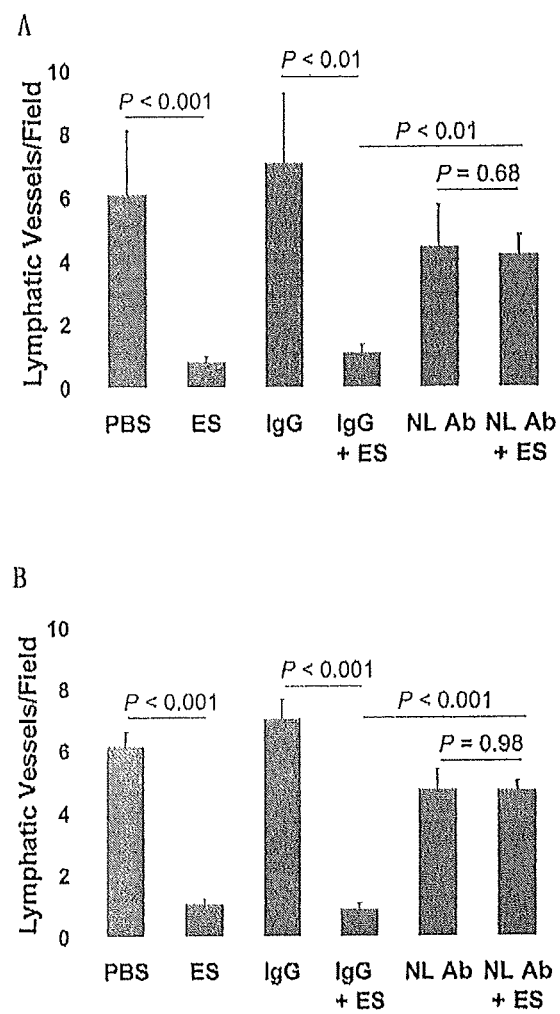
FIG. 9 shows that endostatin inhibits tumor lymphangiogenesis via cell surface nucleolin. A. lymphatic vessel density in B16/F10 melanoma tissues were assessed by Immunofluorescence using anti-podoplanin antibody respectively. B. Quantification of lymphatic vessel density by podoplanin immunofluorescence in orthotopic MDA-MB-231 human breast cancer mouse model. MDA-MB-231 cells were inoculated into the mammary fat pad of nude mice. Mice were intraperitoneally administrated of PBS, control IgG (2 mg/kg), or anti-nucleolin antibody (2 mg/kg) respectively, with or without endostatin (2 mg/kg). 3 weeks after first administration, lymphatic vessel density was analyzed.

In both B16/F10 melanoma (FIG. 9A) and MDA-MB-231 orthotopic breast cancer (FIG. 9B) models, the lymphatic vessels in tumor tissues were immunostained with podoplanin and quantified, which showed a significant lower density in the endostatin treated group as compared with that in control groups. When anti-nucleolin antibody was repeatedly injected to block the cell surface nucleolin, there was no difference between +/−endostatin groups. These results demonstrate that endostatin significantly inhibits tumor lymphangiogenesis, in vivo, which is mediated by its cell surface receptor nucleolin.

Example 11

Distribution of Nucleolin in Different Tissues and Organs

Cell surface nucleolin in normal colon and lymph node of mouse, tumor tissue and lymph node of melanoma bearing mice were detected by standard protocol of immunohistochemistry.

Figure 10:
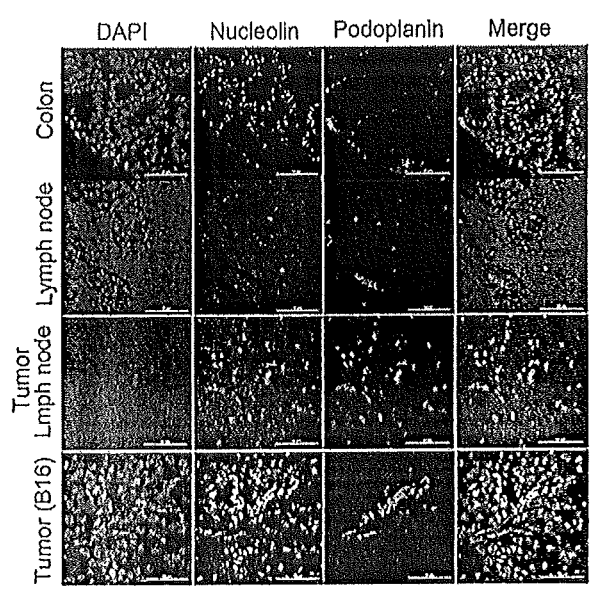
FIG. 10 shows the distribution of nucleolin in different tissues and organs. Immunostaining of nucleolin and lymphatic vessels in colon and lymph node of normal adult mice or melanoma-bearing mice are shown. Blue: DAPI; green: Nucleolin; red: podoplanin.

We failed to detect any cell surface expression of nucleolin on podoplanin-positive lymphatic vessels of normal colon or lymph node in normal adult mice (FIG. 10). In contrast, we observed strong cell surface expression of nucleolin in podoplanin-positive lymphatic vessels in melanoma tissues and in lymph nodes with severe tumor metastasis (FIG. 10). These results demonstrate that cell surface nucleolin is specifically expressed in the tumor-associated lymphatic vessels.

Example 12

Cell Surface Nucleolin is Selectively Expressed in Active Lymphatic Endothelial Cells

Figure 11:
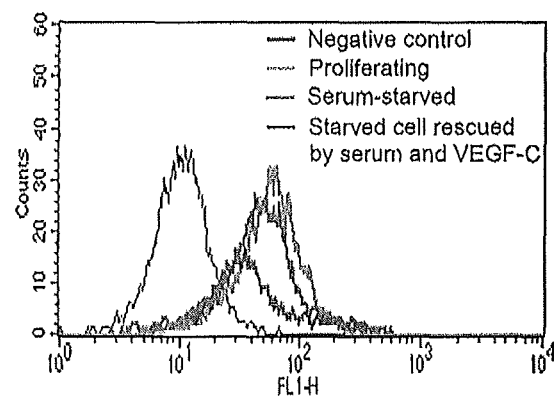
FIG. 11 shows that cell surface nucleolin is selectively expressed in active lymphatic endothelial cells. Cell surface nucleolin was upregulated in lymphangiogenic endothelial cells. Proliferating mLECs were cultured in ECM supplemented with ECGS and 10% FBS. Quiescent mLECs were prepared by serum starvation of proliferating cells for 24 h cultured in ECM without ECGS and serum. The serum and VEGF-C rescued mLECs were prepared by addition of VEGF-C (100 ng/mL) and serum (1%) into the quiescent mLECs for 12 h. Cell surface nucleolin was analyzed by FACS.

Isolated mLECs were starved for 24 h to mimic the quiescent state. Flow cytometric analysis revealed that the amount of cell surface nucleolin was dramatically down-regulated on starved mLECs, while 12 h stimulation with serum and VEGF-C could partially restored the amount of cell surface nucleolin (FIG. 11). This observation is consistent with the in vivo results of Example 11.

So the current invention discovered a new biomarker for lymphangiogenic vessels and active lymphatic endothelial cells.

Example 13

Endostatin does not Affect Quiescent or Mature Adult Lymphatic Vessels

BALB/c normal adult mice (female, 6-8 weeks old, 5 per group) were intraperitoneally injected with endostatin (2 mg/kg) or PBS every other day. After 3 weeks, mice were sacrificed. Lymphatic vessels in colon and lymph node were evaluated by immunohistochemistry.

Figure 12:
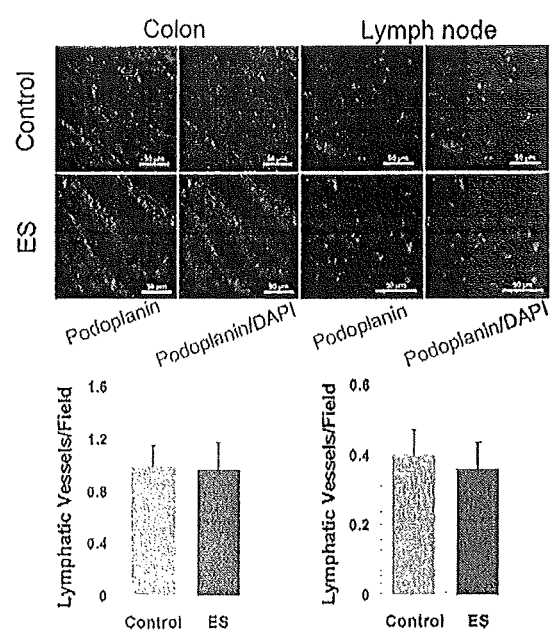
FIG. 12 shows that endostatin does not affect quiescent or mature adult lymphatic vessels. Normal adult BALB/c mice (female, 8-10 weeks old, 5 per group) were treated with endostatin (2 mg/Kg) or PBS for three weeks. Lymphatic vessels in the colon and lymph node of mice were analyzed by immunofluorescence staining of podoplanin. Quantification of lymphatic vessel density for each organ is presented.

Quantitative analysis of colon and lymph node tissues by podoplanin immunofluorescence revealed no significant differences between endostatin treated and PBS treated mice. Besides, the lymphatic structure in treated mice remained normal (FIG. 12).

This suggests that endostatin does not affect quiescent or mature adult lymphatic vessels, which is consistent with the lack of expression of cell surface nucleolin on these vessels. More importantly, this also explains the low toxicity of endostatin in clinical trials [Herbst R S, Hess K R, Tran H T, et al. Phase I study of recombinant human endostatin in patients with advanced solid tumors. J Clin Oncol 2002; 20: 3792-3803].

Example 14

Systemic Blockade of Cell Surface Nucleolin Abrogates the Anti-Lymphatic Metastasis Function of Endostatin on B16/F10 Melanoma Model

B16/F10 melanoma model was performed according to the protocol in Example 9, and 4-6 axillary and inguinal lymph nodes were dissected from each mouse and photographed. Harvest lymph nodes were fixed in formalin for paraffin embedding and immunohistochemical analysis.

Figure 13:
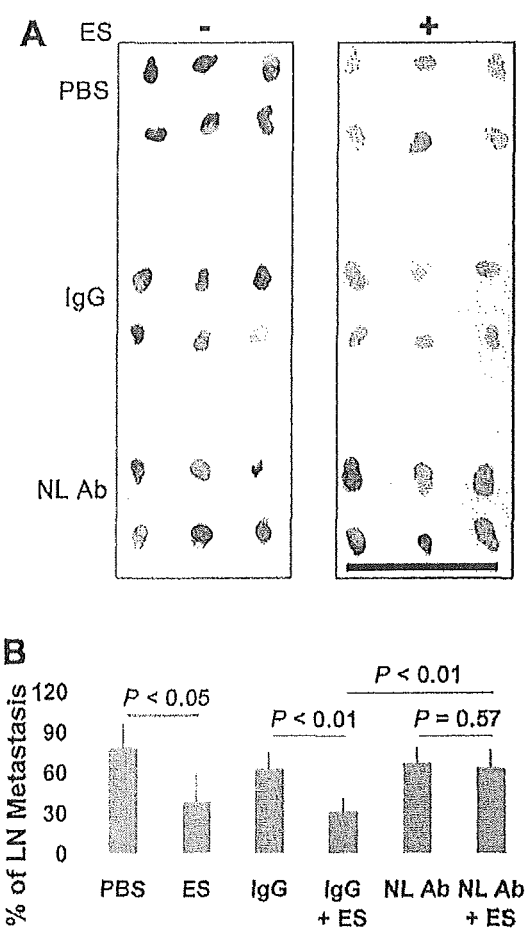
FIG. 13 shows that systemic blockade of cell surface nucleolin abrogates the anti-lymphatic metastasis function of endostatin on B16/F10 melanoma model. A. Axillary and inguinal lymph nodes were removed from B16/F10 melanoma bearing C57 mice. Dissected lymph nodes were photographed. Lymph node with severe melanoma cell metastasis shows black. B. Dissected lymph nodes from each tumor-bearing mice were analyzed (n=5 mice), frequency of lymph nodes with metastasis was quantified. LN: lymph node; T: tumor tissues.

The effects of endostatin on tumor lymph node metastasis after systemic blockade of nucleolin were tested. Autopsy analysis of B16/F10 melanoma model showed that most tumor-bearing mice treated with PBS or control IgG developed metastatic lesions of axillary and inguinal lymph nodes, while endostatin treated group had dramatically reduced lymph nodes metastasis (FIG. 13A) and (B) quantified. Not surprisingly, mice treated with endostatin in combination with anti-nucleolin antibody developed intense axillary and inguinal lymph nodes metastases compared with endostatin plus control IgG group (FIGS. 13A and B). It is obvious that systemic blockade of cell surface nucleolin abrogates the anti-lymphatic metastasis function of endostatin on B16/F10 melanoma model.

Example 15

Figure 14:
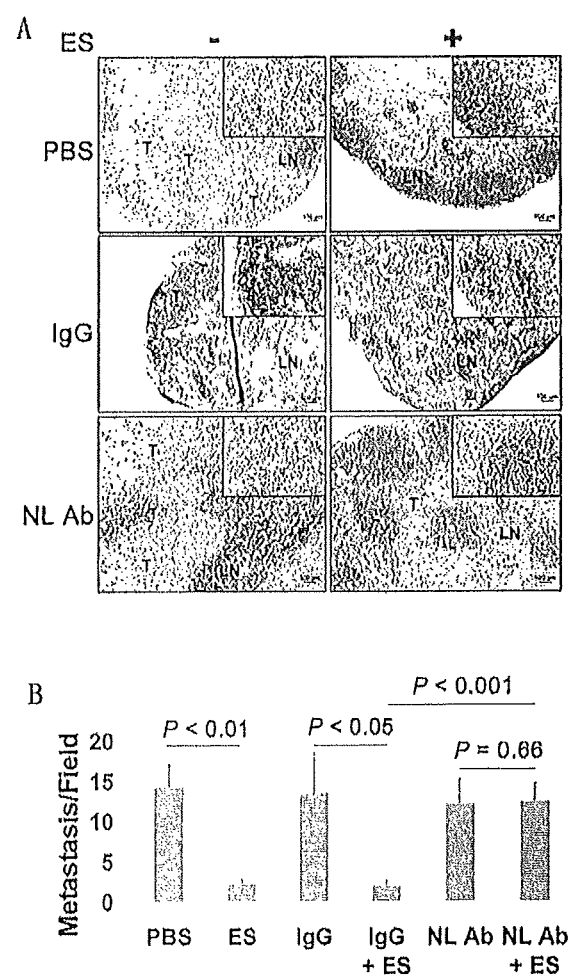
FIG. 14 shows that systemic blockade of cell surface nucleolin abrogates the anti-lymphatic metastasis function of endostatin on orthotopic MDA-MB-231 breast cancer model. A. Inguinal lymph nodes from MDA-MB-231 tumor-bearing mice were dissected. Immunohistochemical examination of dissected lymph nodes was performed with anti-human Ki-67 antibody (brown) and hematoxylin (blue). LN: lymph node tissues; T: tumor tissues. B. Area of Ki-67 positive signals in lymph node with MDA-MB-231 breast cancer metastasis was quantified (n=6 lymph nodes).

Systemic Blockade of Cell Surface Nucleolin Abrogates the Anti-Lymphatic Metastasis Function of Endostatin on Orthotopic MDA-MB-231 Breast Cancer Model Orthotopic MDA-MB-231 breast cancer model was performed according to the protocol in Example 10. Most tumor-bearing mice treated with PBS or control IgG developed metastatic lesions of axillary and inguinal lymph nodes by H&E staining, while endostatin treated group had dramatically reduced lymph nodes metastasis (FIG. 14A) and (B) quantified. While mice treated with endostatin in combination with anti-nucleolin antibody developed intense axillary and inguinal lymph nodes metastases compared with endostatin plus control IgG group (FIGS. 14A and B). Analysis of metastasis to the axillary and inguinal lymph nodes showed no difference between anti-nucleolin antibody and endostatin plus anti-nucleolin antibody group (FIG. 14A), as quantified by the area of human Ki-67-positive signals (FIG. 14B).

It can be concluded that systemic blockade of cell surface nucleolin abrogates the anti-lymphatic metastasis function of endostatin on orthotopic MDA-MB-231 breast cancer model.

Example 16

Figure 15:
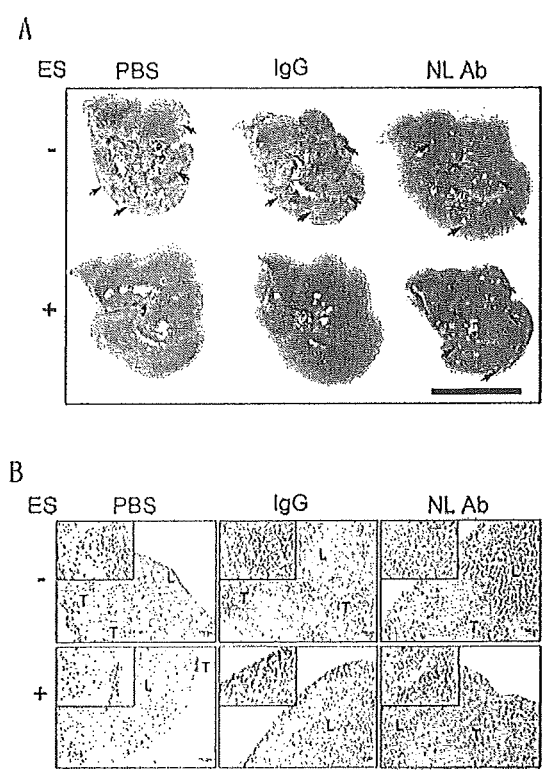
FIG. 15 shows that systemic blockade of cell surface nucleolin abrogates the inhibitory effect of endostatin on the liver metastasis in orthotopic MDA-MB-231 breast cancer model. A. Orthotopic MDA-MB-231 breast cancer model was performed as described in methods. Livers from tumor-bearing mice were dissected and photographed. Arrow means the tumor metastasis site. B. Histochemical analysis of livers from mice in MDA-MB-231 breast cancer model. L=Liver; T=Tumor metastasis site.

Systemic Blockade of Cell Surface Nucleolin Abrogates the Inhibitory Effect of Endostatin on the Liver Metastasis in Orthotopic MDA-MB-231 Breast Cancer Model Using the same batch of orthotopic MDA-MB-231 breast cancer model in Example 15, harvested livers in endostatin-treated mice showed significantly reduced micro-metastatic sites, while the control ones suffered from severe liver metastasis. Consistently, anti-nucleolin antibody abolished the activity of endostatin compared with the control IgG (FIG. 15A). Histochemical analysis of livers from tumor-bearing mice showed similar results (FIG. 15B).

In summary, these results demonstrate that endostatin blocks lymph node metastasis via cell surface nucleolin on tumor lymphatic vessels, which contributes to the reduced metastasis of distant organ.

All animal studies were performed according to the Beijing administration office of laboratory animal for the care and use of laboratory animals. Human tumor specimen sections were prepared with the approval of the Scientific Investigation Board of Tsinghua University.

Data are presented as mean. Statistical analyses were assessed by a two-tailed Student's t test.

Example 17

Figure 16:
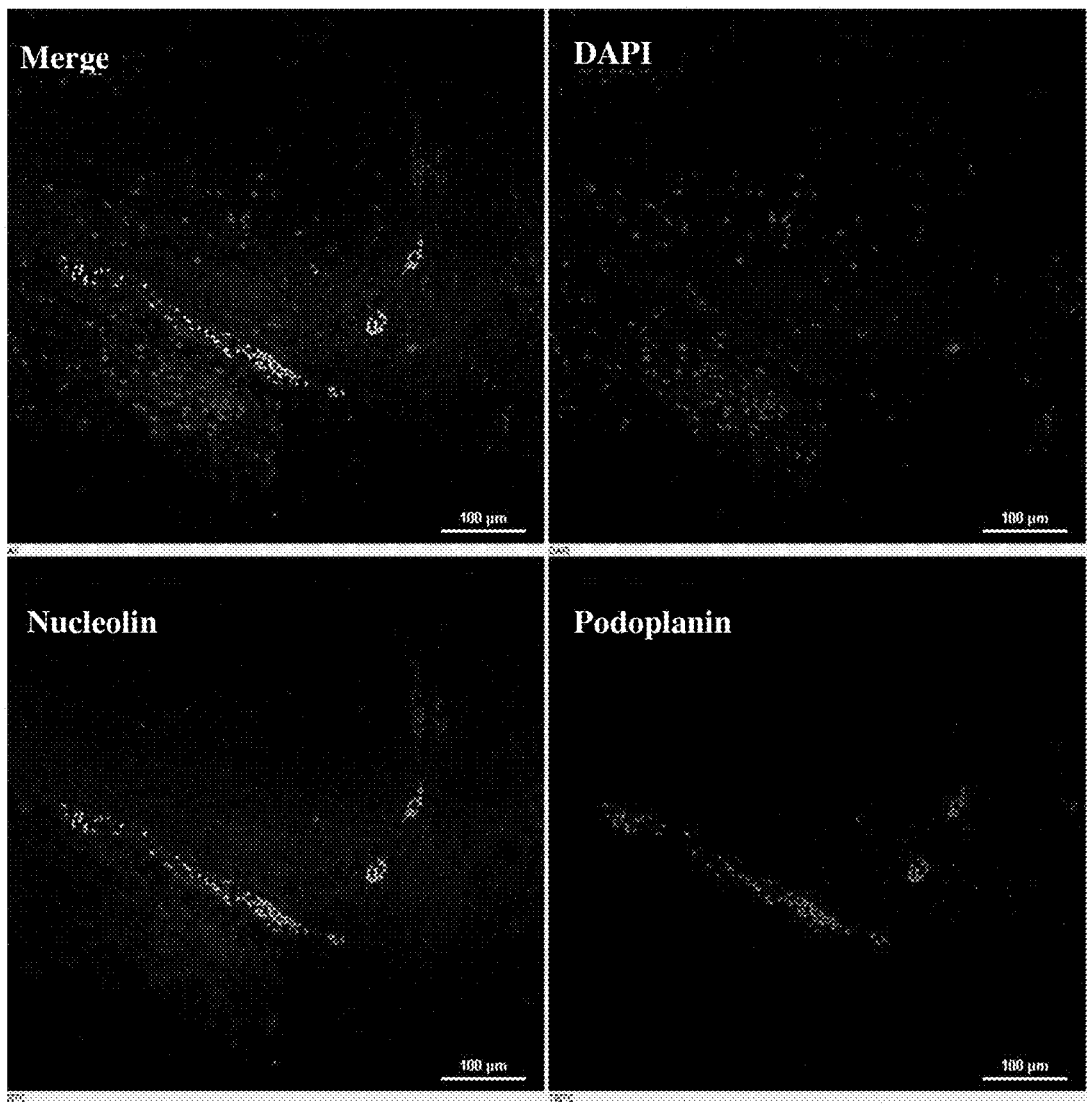
FIG. 16 shows the detection of nucleolin in mediastinal lymph nodes from lung cancer patients. Red stands for lymphatic vessels. Nucleolin was stained in green color and DAPI serves as the marker of nuclei.
Figure 16:
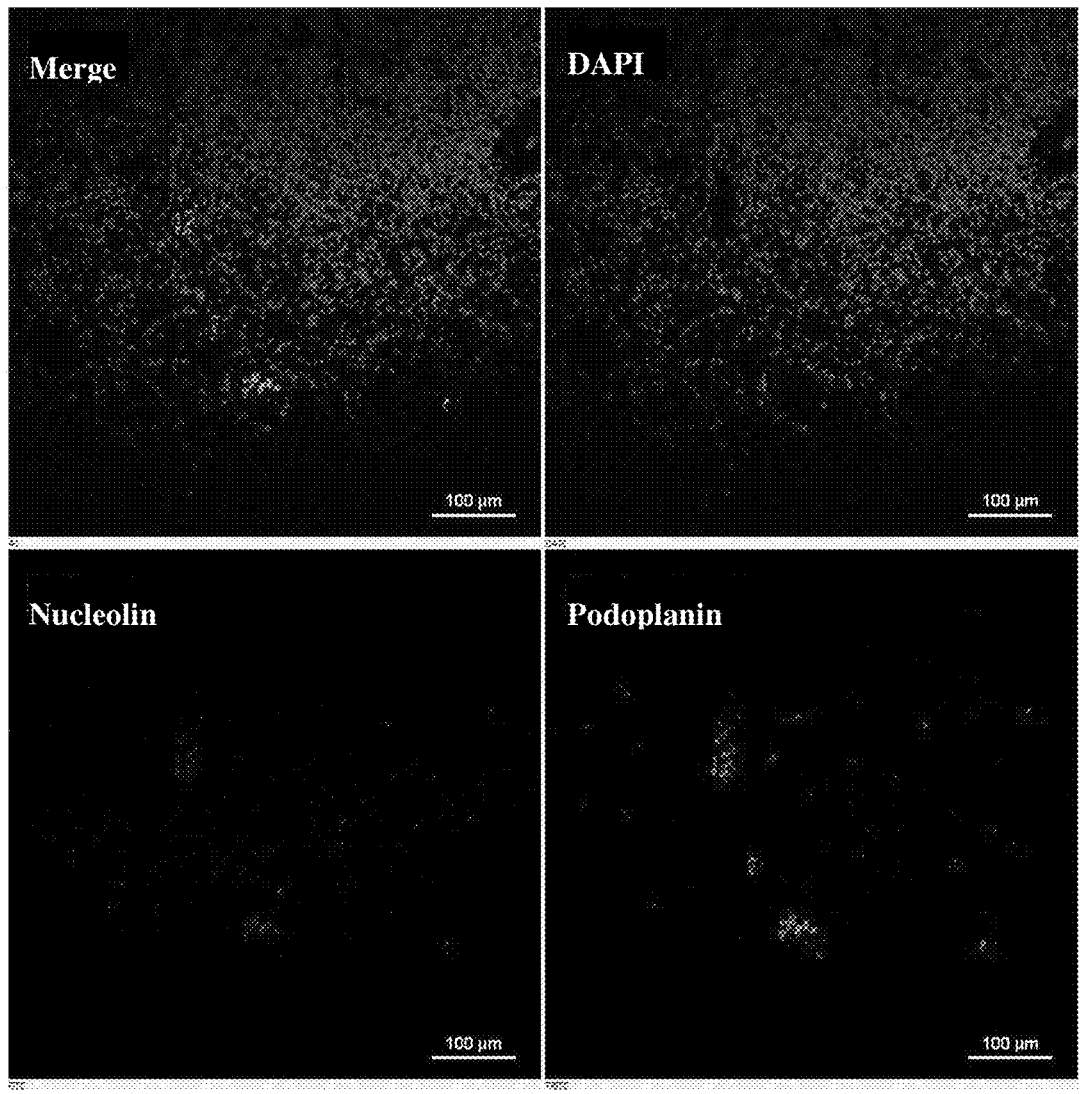
Figure 16:
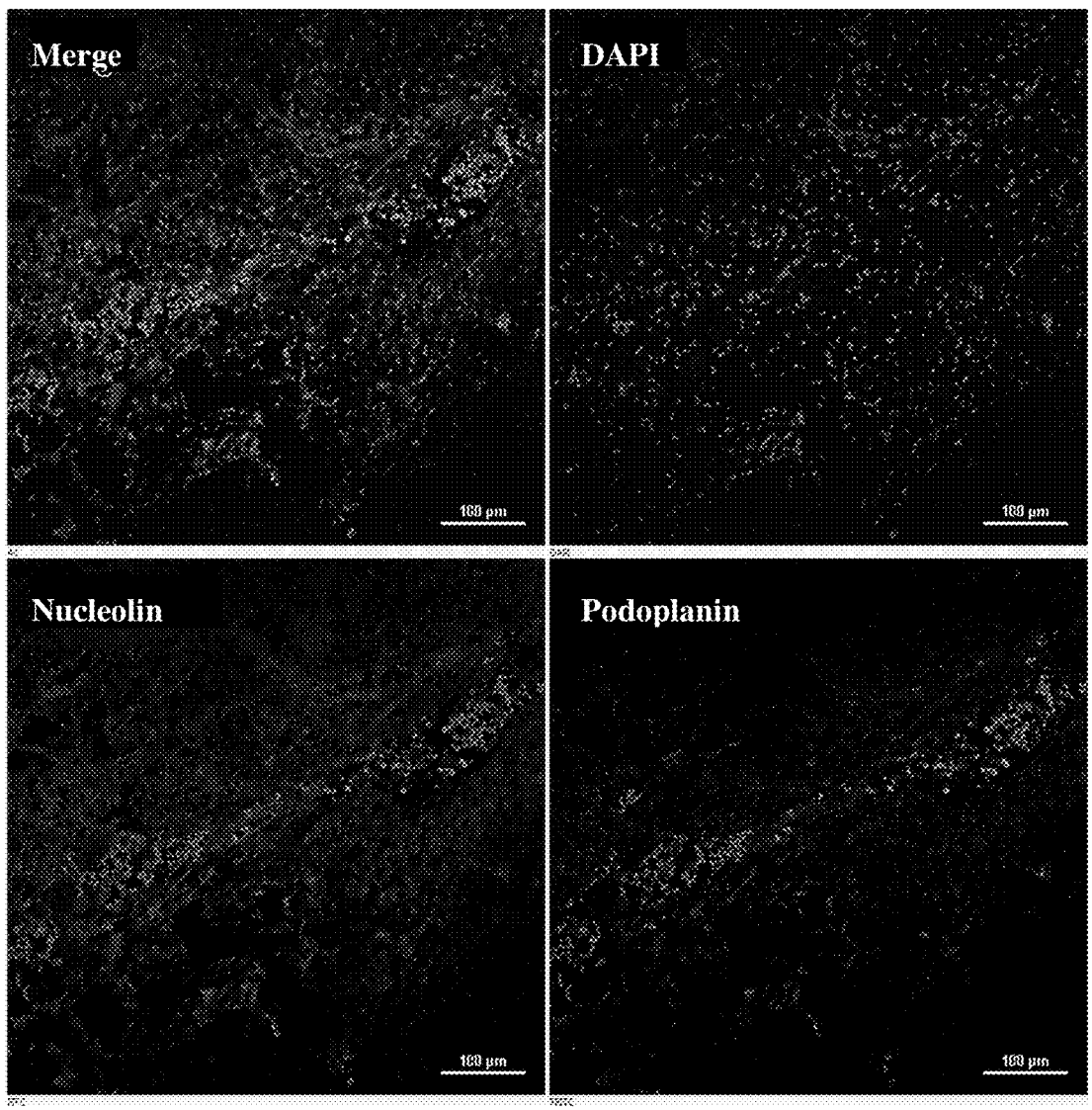

Expression of Nucleolin in Mediastinal Lymph Nodes from Lung Cancer Patients Suggests a Higher Risk of Metastasis Paraffin sections (5 μm) of the mediastinal lymph nodes from lung cancer patients were blocked using goat serum. Primary mouse anti-nucleolin monoclonal antibody and rat anti-podoplanin monoclonal antibody were used to label nucleolin and lymphatic vessels, respectively, which were then detected by FITC-labeled goat anti-mouse IgG and TRITC labeled goat anti-rat IgG secondary antibodies. Nuclei were stained with DAPI. NIKON A1 confocal microscope was employed to take photographs, of which representative fields are shown in FIG. 16: (A) Case 1 shows that in a positive lymph node with metastatic cancer cells, nucleolin (green) co-localize with lymphatic vessels (red), and the expression level of nucleolin is high; (B) Case 2 shows that in a negative lymph node without metastatic cancer cell, the expression level of nucleolin (green) is low, and this patient has obtained progression free survival (PFS) for over 2 years; (C) Case 3 shows a negative lymph node without metastatic cancer cell, in which nucleolin was highly expressed and co-localized with lymphatic vessels. Metastasis was detected with this patient six months after the surgery.

Cells and Reagents

B16/F10 and MDA-MB-231 cell lines were purchased from the American Type Culture Collection (Manassas, Va.). E. coli expressed recombinant wild type endostatin, and rabbit polyclonal antibodies against endostatin were from Protgen (Beijing, China). Control rabbit IgG and the polyclonal rabbit antibody against nucleolin were from our lab stock [Shi H, Huang Y, Zhou H, et al. Nucleolin is a receptor that mediates antiangiogenic and antitumor activity of endostatin. Blood 2007; 110: 2899-2906; Huang Y, Shi H, Zhou H, et al. The angiogenic function of nucleolin is mediated by vascular endothelial growth factor and non-muscle myosin. Blood 2006; 107: 3564-3571]. Commercial rabbit-polyclonal-antibody against nucleolin was from Abcam (Cambridge, UK). Rabbit antibody against PECAM-1 was from Bioworld Technology, inc. (USA). Rabbit antibody against mouse LYVE-1 was from RELIAtech (Germany). Antibodies against actin, podoplanin, VEGFR-3, TRITC or FITC-conjuncted secondary antibodies to rabbit, mouse, goat and hamster IgG were from Santa Cruz Biotechnology (Santa Cruz, Calif., USA). Recombinant VEGF-C was from R&D Systems, Inc. (USA). Endothelial cell culture medium (ECM) supplemented with endothelial cell growth supplement (ECGS) was from Sciencell (USA). Goat anti-rabbit IgG conjuncted microbeads for Magnetic cell sorting (MCS) were form Miltenyi Biotec (Germany).

We claim:

1. A method of treating a cancer subject having or suspected to have lymphatic metastasis, comprising the steps of:
a) determining the presence of cell surface nucleolin on lymphatic vessels in a cancer tissue sample or a tissue sample from lymph node adjacent to the cancer tissue from said subject, and
b) administering a therapeutically effective amount of endostatin to said subject if said subject is determined as positive for the presence of cell surface nucleolin on lymphatic vessels in the sample.

2. A method of preventing lymphatic metastasis in a cancer subject, comprising the steps of determining the presence of cell surface nucleolin on lymphatic vessels in a cancer tissue sample or a tissue sample from lymph node adjacent to the cancer tissue from said subject, and administering a therapeutically effective amount of endostatin to said subject if said subject is determined as positive for the presence of cell surface nucleolin on lymphatic vessels in the sample.

3. A method of preventing or inhibiting the proliferation and/or migration of lymphatic endothelial cells in a cancer subject, comprising the steps of determining the presence of cell surface nucleolin on lymphatic vessels in a cancer tissue sample or a tissue sample from lymph node adjacent to the cancer tissue from said subject, and administering a therapeutically effective amount of endostatin to said subject if said subject is determined as positive for the presence of cell surface nucleolin on lymphatic vessels in the sample.

4. The method of claim 1, wherein the endostatin is in form of a conjugate.

5. The method of claim 4, wherein the endostatin is covalently linked to a modifier capable of enhancing its half-life and/or biological activity.

6. The method of claim 5, wherein the modifier is a PEG molecule.

7. The method of claim 6, wherein the PEG molecule is covalently linked to the N-terminal amino group of the endostatin.

8. The method of claim 7, wherein the PEG molecule has a molecular weight of 20-40 kD.

9. The method of claim 4, wherein the endostatin is linked to a cytotoxic agent.

10. A method of treating a cancer subject after surgical removal of cancer lesion, wherein the cancer subject has negative lymph nodes without metastatic cancer cell, comprising:
 (i) determining the presence of cell surface nucleolin on lymphatic vessels in a cancer tissue sample or a tissue sample from lymph node adjacent to the cancer tissue from said subject,
 (ii) determining the likelihood of lymphatic metastasis of said subject, wherein the presence of cell surface nucleolin on lymphatic vessels in the cancer tissue sample or the lymph node tissue sample is indicative of high likelihood of lymphatic metastasis in said subject, and
 (iii) administering a therapeutic effective amount of endostatin to said subject if said subject is determined as positive for the presence of cell surface nucleolin on lymphatic vessels in the cancer tissue sample or the lymph node tissue sample.

11. The method of claim 2, wherein the endostatin is in form of a conjugate.

12. The method of claim 11, wherein the endostatin is covalently linked to a modifier capable of enhancing its half-life and/or biological activity.

13. The method of claim 12, wherein the modifier is a PEG molecule.

14. The method of claim 3, wherein the endostatin is in form of a conjugate.

15. The method of claim 14, wherein the endostatin is covalently linked to a modifier capable of enhancing its half-life and/or biological activity.

16. The method of claim 15, wherein the modifier is a PEG molecule.

17. The method of claim 16, wherein the PEG molecule is covalently linked to the Nterminal a amino group of the endostatin.

18. The method of claim 1, further comprising, before the administering step, determining the susceptibility of the subject to endostatin therapy according to the presence or level of cell surface nucleolin on lymphatic vessels in the sample.

\* \* \* \* \*